United States Patent
Huebner et al.

(10) Patent No.: US 7,153,309 B2
(45) Date of Patent: Dec. 26, 2006

(54) GUIDE SYSTEM FOR BONE-REPAIR DEVICES

(75) Inventors: Randall J. Huebner, Beaverton, OR (US); Steven P. Horst, Dayton, OR (US)

(73) Assignee: Acumed LLC, Hillsboro, OR (US)

( * ) Notice: Subject to any disclaimer, the term of this patent is extended or adjusted under 35 U.S.C. 154(b) by 14 days.

(21) Appl. No.: 10/717,401

(22) Filed: Nov. 19, 2003

(65) Prior Publication Data

US 2004/0102788 A1    May 27, 2004

Related U.S. Application Data

(60) Provisional application No. 60/512,322, filed on Oct. 17, 2003, provisional application No. 60/427,910, filed on Nov. 19, 2002.

(51) Int. Cl.
  *A61B 17/58* (2006.01)
  *A61F 2/00* (2006.01)
(52) U.S. Cl. .................................... 606/96
(58) Field of Classification Search ............ 606/96, 606/98, 70, 71, 97, 53, 86, 69, 72, 73
   See application file for complete search history.

(56) References Cited

U.S. PATENT DOCUMENTS

| | | | |
|---|---|---|---|
| 820,503 A | 5/1906 | Krengel et al. |
| 869,697 A | 10/1907 | Eilhauer et al. |
| 1,105,105 A | 7/1914 | Sherman |
| 1,789,060 A | 1/1931 | Weisenbach |
| 1,889,239 A | 11/1932 | Crowley |
| 2,243,717 A | 5/1941 | Moreira |
| 2,406,832 A | 9/1946 | Hardinge |
| 2,443,363 A | 6/1948 | Townsend et al. |
| 2,489,870 A | 11/1949 | Dzus |
| 2,494,229 A | 1/1950 | Collison |
| 2,500,370 A | 3/1950 | McKibbin |
| 2,526,959 A | 10/1950 | Lorenzo |
| 2,580,821 A | 1/1952 | Nicola |
| 2,583,896 A | 1/1952 | Siebrandt |
| 2,737,835 A | 3/1956 | Herz |
| 2,961,900 A * | 11/1960 | Arthur et al. ............ 269/91 |
| 3,025,853 A | 3/1962 | Mason |

(Continued)

FOREIGN PATENT DOCUMENTS

AU           89750/91         2/1992

(Continued)

OTHER PUBLICATIONS

*LISS: Less Invasive Stabilization System*, Krettek et al., *Dialogue*, p. 3 (with electronic supplement), Jan. 1999.

(Continued)

*Primary Examiner*—Eduardo C. Robert
*Assistant Examiner*—Anuradha Ramana
(74) *Attorney, Agent, or Firm*—Kolisch Hartwell, P.C.

(57) ABSTRACT

A system, including methods, apparatus, components, and kits, for guiding a hole-forming tool and/or a fastener through a bone and then to a bone-repair device that is connected to the bone. In some embodiments, the system may include a guide device including (1) a coupling portion configured to be connected to the bone-repair device adjacent a first surface of a bone; and (2) a guide portion connected to the coupling portion and configured to be disposed adjacent a second surface of the bone that generally opposes the first surface on the bone. The guide portion is configured to guide the at least one hole-forming tool and fastener into the bone and then to a predefined position of the bone-repair device.

17 Claims, 4 Drawing Sheets

U.S. PATENT DOCUMENTS

| | | | |
|---|---|---|---|
| 3,072,423 A | 1/1963 | Charlton | |
| 3,171,518 A | 3/1965 | Bergmann | |
| 3,488,779 A | 1/1970 | Christensen | |
| 3,489,143 A | 1/1970 | Halloran | |
| 3,593,709 A | 7/1971 | Halloran | |
| 3,604,414 A | 9/1971 | Borges | |
| 3,664,022 A * | 5/1972 | Small | 433/75 |
| 3,716,050 A | 2/1973 | Johnston | |
| 3,741,205 A | 6/1973 | Markolf et al. | |
| 3,842,825 A | 10/1974 | Wagner | |
| 3,866,458 A | 2/1975 | Wagner | |
| 3,900,025 A | 8/1975 | Barnes, Jr. | |
| 3,901,064 A | 8/1975 | Jacobson | |
| 3,939,497 A | 2/1976 | Heimke et al. | |
| 3,965,720 A | 6/1976 | Goodwin et al. | |
| 4,187,840 A | 2/1980 | Watanabe | |
| 4,187,841 A | 2/1980 | Knutson | |
| 4,201,215 A | 5/1980 | Crossett et al. | |
| 4,364,382 A | 12/1982 | Mennen | |
| 4,388,921 A | 6/1983 | Sutter et al. | |
| 4,408,601 A | 10/1983 | Wenk | |
| RE31,628 E | 7/1984 | Allgower et al. | |
| 4,457,307 A | 7/1984 | Stillwell | |
| 4,465,065 A | 8/1984 | Gotfried | |
| 4,484,570 A | 11/1984 | Sutter et al. | |
| 4,493,317 A | 1/1985 | Klaue | |
| 4,498,468 A | 2/1985 | Hansson | |
| 4,506,681 A | 3/1985 | Mundell | |
| 4,513,744 A | 4/1985 | Klaue | |
| 4,565,191 A | 1/1986 | Slocum | |
| 4,565,192 A | 1/1986 | Shapiro | |
| 4,565,193 A | 1/1986 | Streli | |
| 4,573,458 A | 3/1986 | Lower | |
| 4,651,724 A | 3/1987 | Berentey et al. | |
| 4,683,878 A | 8/1987 | Carter | |
| 4,703,751 A | 11/1987 | Pohl | |
| 4,708,139 A * | 11/1987 | Dunbar, IV | 606/96 |
| 4,718,413 A | 1/1988 | Johnson | |
| 4,730,608 A | 3/1988 | Schlein | |
| 4,733,654 A * | 3/1988 | Marino | 606/64 |
| 4,736,737 A | 4/1988 | Fargie et al. | |
| 4,743,261 A | 5/1988 | Epinette | |
| 4,750,481 A | 6/1988 | Reese | |
| 4,757,810 A | 7/1988 | Reese | |
| 4,759,350 A | 7/1988 | Dunn et al. | |
| 4,760,843 A | 8/1988 | Fischer et al. | |
| 4,794,918 A | 1/1989 | Wolter | |
| 4,800,874 A | 1/1989 | David et al. | |
| 4,823,780 A | 4/1989 | Odensten et al. | |
| 4,865,025 A * | 9/1989 | Buzzi et al. | 606/96 |
| 4,867,144 A | 9/1989 | Karas et al. | |
| 4,892,093 A | 1/1990 | Zarnowski et al. | |
| 4,893,619 A | 1/1990 | Dale et al. | |
| 4,895,141 A | 1/1990 | Koeneman et al. | |
| 4,903,691 A | 2/1990 | Heinl | |
| 4,917,604 A | 4/1990 | Small | |
| 4,923,471 A | 5/1990 | Morgan | |
| 4,926,847 A | 5/1990 | Luckman | |
| 4,943,292 A | 7/1990 | Foux | |
| 4,955,886 A | 9/1990 | Pawluk | |
| 4,957,497 A | 9/1990 | Hoogland et al. | |
| 4,963,153 A | 10/1990 | Noesberger et al. | |
| 4,964,403 A | 10/1990 | Karas et al. | |
| 4,966,599 A | 10/1990 | Pollock | |
| 4,973,332 A | 11/1990 | Kummer | |
| 4,988,350 A | 1/1991 | Herzberg | |
| 5,002,544 A | 3/1991 | Klaue et al. | |
| 5,006,120 A | 4/1991 | Carter | |
| 5,013,315 A | 5/1991 | Barrows | |
| 5,015,248 A | 5/1991 | Burstein et al. | |
| 5,041,113 A | 8/1991 | Biedermann et al. | |
| 5,042,983 A | 8/1991 | Rayhack | |
| 5,049,149 A | 9/1991 | Schmidt | |
| 5,053,036 A | 10/1991 | Perren et al. | |
| 5,085,660 A | 2/1992 | Lin | |
| 5,113,685 A | 5/1992 | Asher et al. | |
| 5,129,899 A | 7/1992 | Small et al. | |
| 5,133,718 A | 7/1992 | Mao | |
| 5,139,497 A | 8/1992 | Tilghman et al. | |
| 5,147,361 A | 9/1992 | Ojima et al. | |
| 5,151,103 A | 9/1992 | Tepic et al. | |
| 5,154,717 A | 10/1992 | Matsen, III et al. | |
| 5,161,404 A | 11/1992 | Hayes | |
| 5,176,685 A | 1/1993 | Rayhack | |
| 5,190,544 A | 3/1993 | Chapman et al. | |
| 5,190,545 A | 3/1993 | Corsi et al. | |
| 5,197,966 A | 3/1993 | Sommerkamp | |
| 5,201,737 A | 4/1993 | Leibinger et al. | |
| 5,217,441 A * | 6/1993 | Shichman | 604/536 |
| 5,234,431 A | 8/1993 | Keller | |
| 5,236,432 A | 8/1993 | Matsen, III et al. | |
| 5,269,784 A | 12/1993 | Mast | |
| 5,290,288 A | 3/1994 | Vignaud et al. | |
| 5,304,180 A | 4/1994 | Slocum | |
| 5,314,490 A | 5/1994 | Wagner et al. | |
| 5,356,410 A * | 10/1994 | Pennig | 606/62 |
| 5,364,398 A | 11/1994 | Chapman et al. | |
| 5,364,399 A * | 11/1994 | Lowery et al. | 606/69 |
| 5,380,327 A | 1/1995 | Eggers et al. | |
| 5,413,577 A | 5/1995 | Pollock | |
| 5,423,826 A * | 6/1995 | Coates et al. | 606/96 |
| 5,429,641 A * | 7/1995 | Gotfried | 606/67 |
| 5,443,516 A | 8/1995 | Albrektsson et al. | |
| 5,458,654 A * | 10/1995 | Tepic | 623/23.27 |
| 5,468,242 A | 11/1995 | Reisberg | |
| 5,474,553 A | 12/1995 | Baumgart | |
| 5,487,741 A | 1/1996 | Maruyama et al. | |
| 5,487,743 A | 1/1996 | Laurain et al. | |
| 5,522,902 A | 6/1996 | Yuan et al. | |
| 5,527,311 A | 6/1996 | Proctor et al. | |
| 5,531,745 A | 7/1996 | Ray | |
| 5,534,027 A | 7/1996 | Hodorek | |
| 5,545,228 A | 8/1996 | Kambin | |
| 5,564,302 A | 10/1996 | Watrous | |
| 5,578,036 A | 11/1996 | Stone et al. | |
| 5,586,985 A | 12/1996 | Putnam et al. | |
| 5,591,166 A | 1/1997 | Bernhardt et al. | |
| 5,601,553 A | 2/1997 | Trebing et al. | |
| 5,601,565 A | 2/1997 | Huebner | |
| 5,607,426 A | 3/1997 | Ralph et al. | |
| 5,613,971 A * | 3/1997 | Lower et al. | 606/96 |
| 5,643,261 A | 7/1997 | Schafer et al. | |
| 5,643,265 A | 7/1997 | Errico et al. | |
| 5,647,872 A | 7/1997 | Gilbert et al. | |
| 5,658,283 A | 8/1997 | Huebner | |
| 5,662,655 A | 9/1997 | Laboureau et al. | |
| 5,665,088 A | 9/1997 | Gil et al. | |
| 5,665,089 A | 9/1997 | Dall et al. | |
| 5,674,222 A | 10/1997 | Berger et al. | |
| 5,676,666 A * | 10/1997 | Oxland et al. | 606/61 |
| 5,676,667 A | 10/1997 | Hausman | |
| 5,681,313 A | 10/1997 | Diez | |
| 5,697,933 A * | 12/1997 | Gundlapalli et al. | 606/96 |
| 5,702,396 A | 12/1997 | Hoenig et al. | |
| 5,707,372 A | 1/1998 | Errico et al. | |
| 5,707,373 A | 1/1998 | Sevrain et al. | |
| 5,709,682 A | 1/1998 | Medoff | |
| 5,709,686 A * | 1/1998 | Talos et al. | 606/69 |
| 5,718,704 A | 2/1998 | Medoff | |
| 5,718,705 A | 2/1998 | Sammarco | |
| 5,720,502 A | 2/1998 | Cain | |
| 5,722,976 A | 3/1998 | Brown | |
| 5,730,743 A | 3/1998 | Kirsch et al. | |
| 5,733,287 A | 3/1998 | Tepic et al. | |

| Patent No. | Date | Name |
|---|---|---|
| 5,735,853 A | 4/1998 | Olerud |
| 5,741,258 A | 4/1998 | Klaue et al. |
| 5,741,259 A | 4/1998 | Chan |
| 5,749,872 A | 5/1998 | Kyle et al. |
| 5,749,873 A | 5/1998 | Fairley |
| 5,752,958 A | 5/1998 | Wellisz |
| 5,766,174 A * | 6/1998 | Perry .................. 606/62 |
| 5,772,662 A | 6/1998 | Chapman et al. |
| 5,807,396 A | 9/1998 | Raveh |
| 5,810,823 A | 9/1998 | Klaue et al. |
| 5,810,824 A | 9/1998 | Chan |
| 5,853,413 A | 12/1998 | Carter et al. |
| D404,128 S | 1/1999 | Huebner |
| 5,855,580 A | 1/1999 | Kreidler et al. |
| 5,871,548 A | 2/1999 | Sanders et al. |
| 5,879,389 A | 3/1999 | Koshino |
| 5,902,304 A | 5/1999 | Walker et al. |
| 5,904,683 A | 5/1999 | Pohndorf et al. |
| 5,916,216 A | 6/1999 | DeSatnick et al. |
| 5,919,195 A | 7/1999 | Wilson et al. |
| 5,928,234 A | 7/1999 | Manspeizer |
| 5,931,839 A | 8/1999 | Medoff |
| 5,938,664 A | 8/1999 | Winquist et al. |
| 5,941,878 A | 8/1999 | Medoff |
| 5,951,557 A | 9/1999 | Luter |
| 5,954,722 A | 9/1999 | Bono |
| 5,964,763 A | 10/1999 | Incavo et al. |
| 5,968,047 A | 10/1999 | Reed |
| 5,973,223 A | 10/1999 | Tellman et al. |
| 6,001,099 A | 12/1999 | Huebner |
| 6,004,323 A | 12/1999 | Park et al. |
| 6,022,350 A | 2/2000 | Ganem |
| 6,053,915 A | 4/2000 | Bruchmann |
| 6,077,266 A | 6/2000 | Medoff |
| 6,077,271 A | 6/2000 | Huebner et al. |
| 6,096,040 A | 8/2000 | Esser |
| 6,096,043 A | 8/2000 | Techiera et al. |
| 6,113,603 A | 9/2000 | Medoff |
| 6,117,160 A | 9/2000 | Bonutti |
| 6,123,709 A | 9/2000 | Jones |
| 6,129,728 A | 10/2000 | Schumacher et al. |
| 6,129,730 A * | 10/2000 | Bono et al. ................ 606/73 |
| 6,139,548 A | 10/2000 | Errico |
| 6,152,927 A | 11/2000 | Farris et al. |
| 6,179,839 B1 | 1/2001 | Weiss et al. |
| 6,183,475 B1 | 2/2001 | Lester et al. |
| 6,193,721 B1 | 2/2001 | Michelson |
| 6,197,028 B1 | 3/2001 | Ray et al. |
| 6,206,886 B1 * | 3/2001 | Bennett ................ 606/104 |
| 6,221,073 B1 | 4/2001 | Weiss et al. |
| 6,224,602 B1 | 5/2001 | Hayes |
| 6,228,087 B1 | 5/2001 | Fenaroli et al. |
| 6,235,033 B1 | 5/2001 | Brace et al. |
| 6,235,034 B1 | 5/2001 | Bray |
| 6,238,396 B1 | 5/2001 | Lombardo |
| 6,258,092 B1 | 7/2001 | Dall |
| 6,261,291 B1 | 7/2001 | Talaber et al. |
| 6,273,889 B1 | 8/2001 | Richelsoph |
| 6,283,969 B1 | 9/2001 | Grusin et al. |
| 6,290,703 B1 | 9/2001 | Ganem |
| 6,302,883 B1 | 10/2001 | Bono |
| 6,302,884 B1 | 10/2001 | Wellisz et al. |
| 6,302,887 B1 | 10/2001 | Spranza et al. |
| 6,306,136 B1 | 10/2001 | Baccelli |
| 6,312,431 B1 | 11/2001 | Asfora |
| 6,315,779 B1 | 11/2001 | Morrison et al. |
| 6,322,562 B1 | 11/2001 | Wolter |
| 6,325,803 B1 | 12/2001 | Schumacher et al. |
| 6,331,179 B1 | 12/2001 | Freid et al. |
| 6,336,927 B1 | 1/2002 | Rogozinski |
| 6,338,734 B1 | 1/2002 | Burke et al. |
| 6,342,055 B1 | 1/2002 | Eisermann et al. |
| 6,342,075 B1 | 1/2002 | MacArthur |
| 6,355,036 B1 | 3/2002 | Nakajima |
| 6,355,042 B1 | 3/2002 | Winquist |
| 6,358,250 B1 | 3/2002 | Orbay |
| 6,364,881 B1 | 4/2002 | Apgar et al. |
| 6,364,882 B1 | 4/2002 | Orbay |
| 6,364,883 B1 | 4/2002 | Santilli |
| 6,379,354 B1 | 4/2002 | Rogozinski |
| 6,379,364 B1 | 4/2002 | Brace et al. |
| 6,402,756 B1 | 6/2002 | Ralph et al. |
| 6,413,259 B1 | 7/2002 | Lyons et al. |
| 6,428,542 B1 | 8/2002 | Michelson |
| 6,436,103 B1 | 8/2002 | Suddaby |
| 6,440,135 B1 | 8/2002 | Orbay et al. |
| 6,454,769 B1 | 9/2002 | Wagner et al. |
| 6,454,770 B1 | 9/2002 | Klaue |
| 6,458,133 B1 | 10/2002 | Lin |
| 6,503,250 B1 | 1/2003 | Paul |
| 6,508,819 B1 | 1/2003 | Orbay |
| 6,514,274 B1 | 2/2003 | Boucher et al. |
| 6,520,965 B1 | 2/2003 | Chervitz et al. |
| 6,527,775 B1 | 3/2003 | Warburton |
| 6,533,789 B1 | 3/2003 | Hall, IV et al. |
| 6,540,753 B1 * | 4/2003 | Cohen .................. 606/99 |
| 6,547,790 B1 | 4/2003 | Harkey et al. |
| 6,565,570 B1 | 5/2003 | Sterett et al. |
| 6,592,578 B1 | 7/2003 | Henniges et al. |
| 6,595,993 B1 | 7/2003 | Donno et al. |
| 6,602,255 B1 | 8/2003 | Campbell et al. |
| 6,623,486 B1 | 9/2003 | Weaver et al. |
| 6,623,487 B1 | 9/2003 | Goshert |
| 6,682,531 B1 | 1/2004 | Winquist et al. |
| 6,682,533 B1 | 1/2004 | Dinsdale et al. |
| 6,692,503 B1 * | 2/2004 | Foley et al. .............. 606/96 |
| 6,695,846 B1 | 2/2004 | Richelsoph et al. |
| 6,706,046 B1 | 3/2004 | Orbay et al. |
| 6,712,820 B1 | 3/2004 | Orbay |
| 6,719,759 B1 | 4/2004 | Wagner et al. |
| 6,730,090 B1 | 5/2004 | Orbay et al. |
| 6,736,819 B1 | 5/2004 | Tipirneni |
| 6,767,351 B1 | 7/2004 | Orbay et al. |
| 6,793,658 B1 * | 9/2004 | LeHuec et al. ............. 606/61 |
| 6,858,031 B1 | 2/2005 | Morrison et al. |
| 6,866,665 B1 | 3/2005 | Orbay |
| 6,893,444 B1 | 5/2005 | Orbay |
| 2001/0011172 A1 | 8/2001 | Orbay et al. |
| 2002/0032446 A1 | 3/2002 | Orbay |
| 2002/0055741 A1 | 5/2002 | Schlapfer et al. |
| 2002/0133172 A1* | 9/2002 | Lambrecht et al. ........ 606/130 |
| 2002/0143336 A1 | 10/2002 | Hearn |
| 2002/0143338 A1 | 10/2002 | Orbay et al. |
| 2002/0147453 A1 | 10/2002 | Gambale |
| 2002/0151899 A1 | 10/2002 | Bailey et al. |
| 2002/0156474 A1 | 10/2002 | Wack et al. |
| 2003/0040748 A1* | 2/2003 | Aikins et al. .............. 606/70 |
| 2003/0055429 A1 | 3/2003 | Ip et al. |
| 2003/0083661 A1* | 5/2003 | Orbay et al. .............. 606/69 |
| 2003/0105461 A1 | 6/2003 | Putnam |
| 2003/0149434 A1 | 8/2003 | Paul |
| 2003/0153918 A1 | 8/2003 | Putnam et al. |
| 2003/0233093 A1 | 12/2003 | Moles et al. |
| 2004/0006349 A1* | 1/2004 | Goble et al. ............. 606/104 |
| 2004/0102775 A1 | 5/2004 | Huebner |
| 2004/0102776 A1 | 5/2004 | Huebner |
| 2004/0102777 A1 | 5/2004 | Huebner |
| 2004/0102778 A1 | 5/2004 | Huebner |
| 2004/0116930 A1 | 6/2004 | O'Driscoll et al. |
| 2004/0127901 A1 | 7/2004 | Huebner et al. |
| 2004/0127903 A1 | 7/2004 | Schlapfer et al. |
| 2004/0153073 A1 | 8/2004 | Orbay |
| 2004/0193164 A1 | 9/2004 | Orbay |
| 2004/0193165 A1 | 9/2004 | Orbay |
| 2004/0220566 A1 | 11/2004 | Bray |
| 2004/0260291 A1 | 12/2004 | Jensen |

| | | | |
|---|---|---|---|
| 2004/0260292 | A1 | 12/2004 | Orbay et al. |
| 2004/0260293 | A1 | 12/2004 | Orbay et al. |
| 2004/0260294 | A1 | 12/2004 | Orbay et al. |
| 2004/0260295 | A1 | 12/2004 | Orbay et al. |
| 2005/0049593 | A1 | 3/2005 | Duong et al. |
| 2005/0065520 | A1 | 3/2005 | Orbay |
| 2005/0065522 | A1 | 3/2005 | Orbay |
| 2005/0065523 | A1 | 3/2005 | Orbay |
| 2005/0065524 | A1 | 3/2005 | Orbay |
| 2005/0065528 | A1 | 3/2005 | Orbay |
| 2005/0085818 | A1 | 4/2005 | Huebner |
| 2005/0085819 | A1 | 4/2005 | Ellis et al. |
| 2005/0131413 | A1 | 6/2005 | O'Driscoll et al. |
| 2005/0159747 | A1 | 7/2005 | Orbay |
| 2005/0165395 | A1 | 7/2005 | Orbay et al. |
| 2005/0171544 | A1 | 8/2005 | Falkner |
| 2005/0182405 | A1 | 8/2005 | Orbay et al. |
| 2005/0182406 | A1 | 8/2005 | Orbay et al. |
| 2005/0187551 | A1 | 8/2005 | Orbay et al. |
| 2005/0192578 | A1 | 9/2005 | Horst |
| 2005/0234458 | A1 | 10/2005 | Huebner |
| 2005/0234472 | A1 | 10/2005 | Huebner |

FOREIGN PATENT DOCUMENTS

| | | |
|---|---|---|
| CH | 611 147 | 5/1979 |
| DE | 2515430 | 11/1975 |
| DE | 4201531 | 7/1993 |
| DE | 4343117 | 6/1995 |
| EP | 0 053 999 | 6/1982 |
| EP | 0 410 309 | 1/1991 |
| EP | 0471418 A1 | 2/1992 |
| EP | 0362049 B1 | 5/1992 |
| EP | 1 250 892 A2 | 9/2003 |
| EP | 1 250 892 A3 | 9/2003 |
| FR | 742618 | 3/1933 |
| FR | 2254298 | 7/1975 |
| FR | 2367479 | 5/1978 |
| FR | 2405705 | 5/1979 |
| FR | 2405706 | 5/1979 |
| FR | 2406429 | 5/1979 |
| FR | 2472373 | 7/1981 |
| FR | 2674118 | 9/1992 |
| GB | 2245498 | 1/1992 |
| SU | 610518 | 6/1978 |
| SU | 718097 | 2/1980 |
| SU | 862937 | 9/1981 |
| SU | 897233 | 1/1982 |
| SU | 1049054 | 10/1983 |
| SU | 1130332 | 12/1984 |
| SU | 1192806 | 11/1985 |
| SU | 1223901 | 4/1986 |
| SU | 1225556 | 4/1986 |
| SU | 1544406 | 2/1990 |
| SU | 1630804 | 2/1991 |
| SU | 1644932 | 4/1991 |
| SU | 1683724 | 10/1991 |
| SU | 1711859 A | 2/1992 |
| SU | 1734715 A1 | 5/1992 |
| WO | WO82/01645 | 5/1982 |
| WO | WO87/02572 | 5/1987 |
| WO | WO88/03781 | 6/1988 |
| WO | WO96/29948 | 10/1996 |
| WO | WO97/47251 | 12/1997 |
| WO | WO 0025681 * | 5/2000 |
| WO | WO01/21083 A1 | 3/2001 |
| WO | WO01/62136 A3 | 8/2001 |

OTHER PUBLICATIONS

*Less Invasive Stabilization System Liss*, surgical technique, Synthes/Mathys, Feb. 23, 1999.
*Congruent Plate System*, surgical techinique, Acumed LLC, Dec. 18, 2000.
*Congruent Distal Radius Plate System*, brochure, Acumed LLC, May 1, 2002.
*Internal Fixation in Osteoporotic Bone*, An, p. 276, Jul. 2002.
*AcroPlate*, aap Implantate AG, p. 37, date unknown.
*The Titanium Volar Distal Radius Plate*, Synthes, date unknown.
McBride S.M.O. Stainless Steel Bone Plates brochure, DePuy, Inc., 1943.
Bone Plates brochure, Vitallium, Mar. 1948.
Dupont Distal Humeral Plates brochure, Howmedica Inc., 1990.
The Arnett-TMP* Titanium Miniplating System brochure, Techmedica, Inc., 1989.
Techmedica Bioengineers Keep Tabs on Your Needs brochure, Techmedica, Inc., 1991.
*Biological Plating: A New Concept to Foster Bone Healing*, Synthes (USA), 1991.
*A Comparison of Unicortical and Bicortical End Screw Attachment of Fracture Fixation Plates*, Beaupre et al., *Journal of Orthopaedic Trauma*, vol. 6, No. 3, pp. 294-300, 1992.
Ace 4.5/5.0 mm Titanium Cannulated Screw and Reconstruction Plate System surgical technique brochure, Ace Medical Company, 1992.
Ace 4.5/5.0 mm Titanium Cannulated Screw and Reconstruction Plate System simplified fracture fixation brochure, Ace Medical Company, 1992.
Ace Titanium 3.5/4.0 mm Screw and Plate System with the Ace 3.5 mm Universal Ribbon CT/MRI compatible fixation brochure, Ace Medical Company, 1992.
*Treatment of Three- and Four-Part Fractures of the Proximal Humerus with a Modified Cloverleaf Plate*, Esser, *Journal of Orthopaedic Trauma*, vol. 8, No. 1, pp. 15-22, 1994.
*Treatment by Plates of Anteriorly Displaced Distal Radial Fractures*, Ducloyer, *Fractures of the Distal Radius*, pp. 148-152, 1995.
*Management of Comminuted Distal Radial Fractures*, Jupiter et al., *Fractures of the Distal Radius*, pp. 167-183, 1995.
*Open Reduction of Intra-Articular Fractures of the Distal Radius*, Amadio, *Fractures of the Distal Radius*, pp. 193-202, 1995.
May Anatomical bone Plates: Plates, Bone Screws and Instruments brochure, pp. 3-4 and 10-15, Waldemar Link GmbH & Co., 1995.
Forte Distal Radial Plate System brochure, Zimmer, Inc., 1995.
*Design and Biomechanics of a Plate for the Distal Radius*, Gesensway et al., *Journal of Hand Surgery*, vol. 20, No. 6, pp. 1021-1027, 1995 (abstract only provided).
Ace Symmetry Titanium Upper Extremity Plates surgical technique brochure, Ace Medical Company, 1996.
The Ace Symmetry Titanium Upper Extremity Plates new product release brochure, Ace Medical Company, 1996.
*Fractures of the Distal Radius: A Practical Approach to Management*, Fernandez et al., pp. 103-188, 1996.
Titanium Distal Radius Instrument and Implant Set standard contents description pages, Synthes, Mar. 1997.
Small Titanium Plates overview page, Synthes, p. 2a-33, Mar. 1997.
*Prospective Multicenter Trial of a Plate for Dorsal Fixation of Distal Radius Fractures*, Ring et al., *The Journal of Hand Surgery*, vol. 22A, No. 5, pp. 777-784, Sep. 1997.
*Treatment of Displaced Intra-Articular Fractures of the Distal End of the Radius With Plates*, Fitoussi et al., *The Journal of Bone and Joint Surgery*, vol. 79, No. 9, pp. 1303-1312, 1997 (abstract only provided).
The Titanium Distal Radius Plate, technique guide, Synthes (USA), 1997.
TriMed Wrist Fixation System brochure, TriMed, Inc., 1997.
SCS/D Distal Radius Plate System brochure, Avanta Orthopaedics, 1997.
*Biomechanical Evaluation of the Schuhli Nut*, Kolodziej, et al., *Clinical Orthopaedics and Related Research*, vol. 347, pp. 79-85, Feb. 1998.
Congruent Distal Radius Plate System description, Acumed, Inc., Mar. 4, 1998.
*Intra-Articular Fractures of the Distal Aspect of the Radius*, Trumble et al., *Journal of Bone and Joint Surgery*, vol. 80A, No. 4, pp. 582-600, Apr. 1998.

*Complications of the AO/ASIF Titanium Distal Radius Plate System (π Plate) in Internal Fixation of the Distal Radius: A Brief Report,* Kambouroglou et al., *Journal of Hand Surgery,* vol. 23A, No. 4, pp. 737-741, Jul. 1998.

SCS/V Distal Radius Plate Volar brochure, Avanta Orthopaedics, 1998.

*Salvage of Tibial Pilon Fractures Using Fusion of the Ankle with a 90° Cannulated Blade Plate: A Preliminary Report,* Morgan et al., *Foot & Ankle International,* vol. 20, No. 6, pp. 375-378, Jun. 1999.

*Delayed Rupture of the Flexor Pollicis Longus Tendon After Inappropriate Placement of the π Plate on the Volar Surface of the Distal Radius,* Nunley et al., *Journal of Hand Surgery,* vol. 24, No. 6, pp. 1279-1280, Nov. 1999.

*Scaphoid Protocols Using the Acutrak® Bone Screw System*brochure, Toby, published by Acumed, Inc., Dec. 7, 1999.

TiMAX Pe.R.I. Small Fragment Upper Extremity description pages, DePuy ACE Medical Company, 1999.

The Distal Radius Plate Instrument and Implant Set technique guide, Synthes (USA), 1999.

*Outcome Following Nonoperative Treatment of Displaced Distal Radius Fractures in Low-Demand Patients Older Than 60 Years,* Young, *Journal of Hand Surgery,* vol. 25A, No. 1, pp. 19-28, Jan. 2000.

*Comparison of Three Different Plating Techniques for the Dorsum of the Distal Radius: A Biomechanical Study,,* Peine et al., *Journal of Hand Surgery,* vol. 25A, No. 1, pp. 29-33, Jan. 2000.

*Distal Radial Metaphyseal Forces in an Extrinsic Grip Model: Implications for Postfracture Rehabilitation,* Putnam et al., *Journal of Hand Surgery,* vol. 25A, No. 3, pp. 469-475, May 2000.

Single Unit Osteosynthesis brochure, Surfix Technologies, Sep. 2000.

Supracondylar Cable Plate brochure, Biomet Orthopedics, Inc., 2000.

*Principle-Based Internal Fixation of Distal Humerus Fractures,* Sanchez-Sotelo et al., *Techniques in Hand & Upper Extremity Surgery,* vol. 5, No. 4, pp. 179-187, Dec. 2001.

TriMed Wrist Fixation System internet description pages, TriMed, Inc., 2001.

Titanium Distal Radius Plates description page, Synthes (USA), 2001.

Locon-T Distal Radius Plating System case study and surgical method, Wright Medical Technology, Inc., 2001.

Congruent Plate System—The Mayo Clinic Congruent Elbow Plates brochure, Acumed, Inc., May 7, 2002.

Modular Hand System brochure, Acumed, Inc., Aug. 2002.

Modular Hand System brochure, Acumed, Inc., Sep. 2002.

Internal Fixation in Osteoporotic Bone, An, Y.H., p. 83, 2002.

Periarticular Plating System brochure, Zimmer, Inc., 2002.

Jplate Diaphysis Plates for Japanese brochure, Mizuho Co., Ltd., 2002.

*An Axially Mobile Plate for Fracture Fixation,* Abel et al., *Internal Fixation in Osteoporotic Bone,* pp. 279-283, 2002.

*The Use of Interlocked 'Customised' Blade Plates in the Treatment of Metaphyseal Fractures in Patients with Poor Bone Stock,* Palmer et al., *Injury, Int. J. Care Injured,* vol. 31, pp. 187-191, 2002.

3.5 mm LCP™ Proximal Humerus Plate technique guide, Synthes (USA), 2002.

*Open Reduction and Internal Fixation of Unstable Distal Radius Fractures: Results Using the Trimed Fixation System,* Konrath et al., *Journal of Orthopaedic Trauma,* vol. 16, No. 8, pp. 578-585, 2002.

Locon-T Distal Radius Plating System brochure, Wright Medical Technology, Inc., 2002.

*Distal Radius Fracture,* Tornetta, *Journal of Orthopaedic Trauma,* vol. 16, No. 8, pp. 608-611, 2002.

*Comparison of Different Distal Radius Dorsal and Volar Fracture Fixation Plates: A Biomechanical Study,* Osada et al., *Journal of Hand Surgery,* vol. 28A, No. 1, pp. 94-104, Jan. 2003.

Titanium Wire Plate Osteosynthesis System According to Dr. Gahr internet printout, Erothitan Titanimplantate AG, print date Feb. 6, 2003.

*Tendon Function and Morphology Related to Material and Design of Plates For Distal Radius Fracture Fixation: Canine Forelimb Model,* Turner et al., Orthopaedic Research Society, Feb. 2003.

*Fractures of the Distal Aspect of the Radius: Changes in Treatment Over the Past Two Decades,* Simic, *Journal of Bone and Joint Surgery,* vol. 85-A, No. 3, pp. 552-564, Mar. 2003.

*Palmar Plate Fixation of AO Type C2 Fracture of Distal Radius Using a Locking Compression Plate—A Biomechanical Study in a Cadaveric Model,* Leung et al., *Journal of Hand Surgery,* vol. 28B, No. 3, pp. 263-266, Jun. 2003.

*Bilder*internet printout, Martin GmbH & Co. KG, print date Sep. 5, 2003.

International Search Report for PCT Patent Application Serial No. PCT/US03/22904, Dec. 4, 2003.

*The Use of a Locking Custom Contoured Blade Plate for Peri-Articular Nonunions,,* Harvey et al., *Injury, Int. J. Care Injured,* vol. 34, pp. 111-116, 2003.

*Salvage of Distal Tibia Metaphyseal Nonunions With the 90° Cannulated Blade Plate,* Chin et al., *Clinical Orthopaedics and Related Research,* No. 409, pp. 241-249, 2003.

*Functional Outcome and Complications Following Two Types of Dorsal Plating for Unstable Fractures of the Distal Part of the Radius,* Rozental et al., *Journal of Bone and Joint Surgery,* vol. 85, No. 10, pp. 1956-1960, 2003 (abstract only provided).

*Fixation of Unstable Fractures of the Volar Rim of the Distal Radius with a Volar Buttress Pin®,* Hooker et al., 2003.

*Results of Palmar Plating of the Lunate Facet Combined with External Fixation for the Treatment of High-Engery Compression Fractures of the Distal Radius,* Ruch et al., *J. Orthop, Trauma,* Vo. 18, No. 1, pp. 28-33, Jan. 2004.

*Rib Securing Clamped Plate,* internet printout, Sanatmetal, print date Sep. 22, 2004.

*Zespol Bone Screws,* in *Mikromed—Catalogue 2004* (Nov. 2004), available at http://www.mikromed.pl/katalog/Main/main_eng.htm and http://www.mikromed.pl/katalog/zespol_eng/wkrety.htm.

*Zespol Bone Plates,* in *Mikromed—Catalogue 2004* (Nov. 2004), available at http://www.mikromed.pl/katalog/Main/main_eng.htm and http://www.mikromed.pl/katalog/zespol_eng/plytki.htm.

*SmartLock Locking Screw Technology,* advertisement, *The Journal of Hand Surgery,* vol. 30A, No. 1, Jan. 2005.

*Synthes Volar Distal Radius Locking Plate,* internet description page, Orthocopia, LLC, 2004.

*Acromio-Clavicular Plates,* description page, author and date unknown.

*ECT Internal Fracture Fixation,* brochure, Zimmer, Inc., undated.

*ECT Internal Fracture Fixation System,* order information brochure, Zimmer, Inc., undated.

*NexGen Osteotomy System (OS) surgical technique,* brochure, Zimmer, Inc., undated.

*Esser Complete Distal Radius Plate System,* undated.

*Proximal Humerus Fractures operative technique,* Esser, undated.

*Spider™ and Mini-Spider™ Limited Wrist Fusion System* brochure, Kinetics Medical Incorporated, undated.

*Spider™ Limited Wrist Fusion System* brochure, Kinetics Medical Incorporated, undated.

*VAL Plate*description page, US Implants, undated.

*Zuelzer Hook Plates* descripton page, Codman & Shurtleff, Inc., p. 808, undated.

\* cited by examiner

GUIDE SYSTEM FOR BONE-REPAIR DEVICES

CROSS-REFERENCES TO PRIORITY APPLICATIONS

This application is based upon and claims the benefit under 35 U.S.C. § 119(e) of the following U.S. provisional patent applications: Ser. No. 60/427,910, filed Nov. 19, 2002; and Ser. No. 60/512,322, filed Oct. 17, 2003. Each of these provisional patent applications is incorporated herein by reference in its entirety for all purposes.

CROSS-REFERENCES TO OTHER APPLICATIONS

This application incorporates by reference in their entirety for all purposes the following U.S. patent applications: Ser. No. 10/716,719, filed Nov. 19, 2003, titled ADJUSTABLE BONE PLATES, and naming Randall J. Huebner and Steven P. Horst as inventors; Ser. No. 10/717,402, filed Nov. 19, 2003, titled DEFORMABLE BONE PLATES, and naming Randall J. Huebner as inventor; and Ser. No. 10/717,015, filed Nov. 19, 2003, titled BONE PLATES WITH SLOTS, and naming Randall J. Huebner as inventor; and Ser. No. 10/717,399, filed Nov. 19, 2003, titled BONE PLATES WITH REFERENCE MARKS, and naming Randall J. Huebner as inventor.

This application incorporates by reference in their entirety for all purposes the following U.S. provisional patent applications: Ser. No. 60/427,908, filed Nov. 19, 2002; Ser. No. 60/512,111, filed Oct. 17, 2003; Ser. No. 60/512,136, filed Oct. 17, 2003; and Ser. No. 60/512,323, filed Oct. 17, 2003.

This application incorporates by reference in its entirety for all purposes PCT patent application Ser. No. PCT/US02/18623, filed Jun. 10, 2002.

FIELD OF THE INVENTION

The invention relates to a guide system for bone-repair devices. More specifically, the invention relates to a guide system for guiding a hole-forming tool and/or a fastener through a bone and then to a bone repair device that is connected to the bone.

BACKGROUND

The radius is one of two long bones found in the human forearm. The radius, like other bones, is susceptible to a variety of fractures and other dislocations. For example, distal fractures of the radius are a common result of forward falls, with the palms facing downward, particularly among the elderly. In such falls, force exerted on the distal radius at impact frequently produces dorsal displacement of one or more bone fragments created distal to the fracture site. Unfortunately, internal fixation of such dorsally displaced bone fragments using bone plates has proved problematic.

Fixation may be performed dorsally. In this approach, a surgeon may apply a reducing force on the fracture by attaching a bone plate to the dorsal side of the radius. However, unless the bone plate has a very low profile, dorsal tendons overlying the bone plate may rub against it, producing tendon irritation or even tendon rupture.

Alternatively, fixation may be performed volarly. In this approach, a surgeon may attach a bone plate to the volar side of the radius. The volar side of the radius may be more accessible surgically and defines a distal pocket in which the distal portion of the bone plate may be disposed. Accordingly, the bone plate may be less obtrusive and may produce less tendon irritation with placement, even if the bone plate is thicker and sturdier.

Despite the potential advantages of volar fixation, attachment of the bone plate to the volar side of the fractured radius may complicate reduction of the radius. The distal radius of elderly patients in particular generally contains porous bone of poor quality. Accordingly, bone screws inserted into the distal radius through openings in the bone plate may not achieve enough purchase in the bone to hold distal bone fragments in position against the bone plate. Moreover, these bone screws may be even less effective at gaining enough purchase to pull bone fragments volarly toward the plate to aid in reduction of the fracture. In one alternative volar strategy, a bone plate with threaded openings is employed. Pins having a threaded region near their heads engage the threaded openings to fix the angular positions of the pins relative to the bone plate. These fixed pins are configured to restrict movement of bone fragments through contact with the fragments. However, the pins may be ineffective for pulling bone fragments volarly against the plate and for restricting movement of distal bone fragments after reduction. Thus, there is a need for an alternative strategy for reducing and fixing radial fractures, particularly in the elderly.

SUMMARY OF THE INVENTION

The invention provides systems, including methods, apparatus, components, and kits, for guiding a hole-forming tool and/or a fastener through a bone and then to a bone-repair device that is connected to the bone.

DETAILED DESCRIPTION

The invention provides guide systems, including methods, apparatus, components, and kits, for guiding a hole-forming tool and/or a fastener toward a predefined position(s) of a bone-repair device. The system may be used for coupling the fastener to the bone-repair device, after placement of the fastener through a bone, from an opposing surface of the bone. The bone-repair device may include a bone plate and/or a prosthesis, among others. Accordingly, the guide system may be, for example, a fixation system for fixing a fractured or excised bone, or an implant system for replacing a portion of the bone. The system may include a guide device that connects in a predefined relation to the bone-repair device. The guide device may be configured so that a guide portion of the guide device and the bone-repair device are disposed on generally opposing sides of a bone. The guide device may be configured to correspond to a particular bone-repair device, so that the guide device properly targets hole-forming tools and/or fasteners through the bone and then to predefined position(s) of the bone-repair device.

The guide system may be configured to repair any suitable bone damage, and/or perform any other suitable function, in or on any suitable bone(s). For example, the guide system may be used as a fixation system to reduce and/or fix bone discontinuities, such as fractures or osteotomies of the radius, tibia, fibula, femur, ulna, humerus, pelvis, scapula, vertebrae, cranium, and/or bones of the hand or foot, among others. This fixation system may provide attachment of a bone plate to two or more portions of a bone. In some embodiments, the fixation system may position a bone plate to span a bone joint, for example, to facilitate attachment of the bone plate to two or more bones. In some embodiments, the guide system may be used as an implant system to attach a prosthesis to any suitable bone, such as those recited above.

The following sections describe further aspects of the invention, including, among others, (I) an exemplary system, (II) bone-repair devices, (III) guide devices, (IV) hole-forming tools, (V) fasteners, and (VI) examples.

I. Exemplary System

This section describes an exemplary guide system, in accordance with aspects of the invention. The exemplary system is described in the context of fracture repair for the distal radius; however, as noted elsewhere, the systems provided by the invention may be used for any suitable purpose, with any suitable bone.

Figure 1:
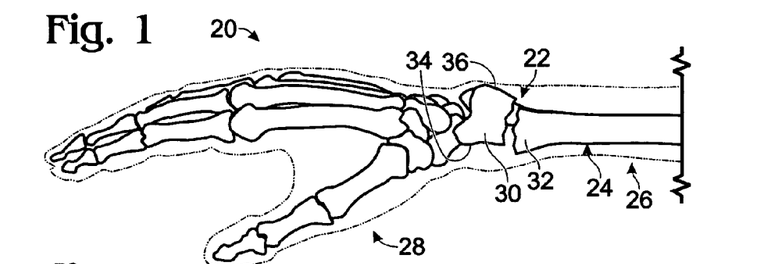
FIG. 1 is a lateral view of the bones of the right hand and distal forearm in which the radius has suffered a Colles' fracture, displacing a distal fragment of the radius dorsally.

FIG. 1 shows an upper right extremity 20 exhibiting a Colles' fracture 22, which is a very common fracture of the distal radius 24 typically caused by using an outstretched hand to break a fall. The position of the fracture is indicated relative to the skin of the distal forearm 26 and hand 28, which is shown in phantom outline. In Colles' fracture 22, a smaller, distal bone fragment 30 may be displaced dorsally from a larger, proximal bone segment 32 of the radius. Colles' fracture 22 may be reduced and fixed with the guide system described herein by placement of a bone plate on the volar (anterior or lower) side 34 of the radius. This placement may reduce or avoid tendon irritation that may occur with flexion when the bone plate is attached to the dorsal (posterior or upper) side 36 of the radius.

Figure 2:
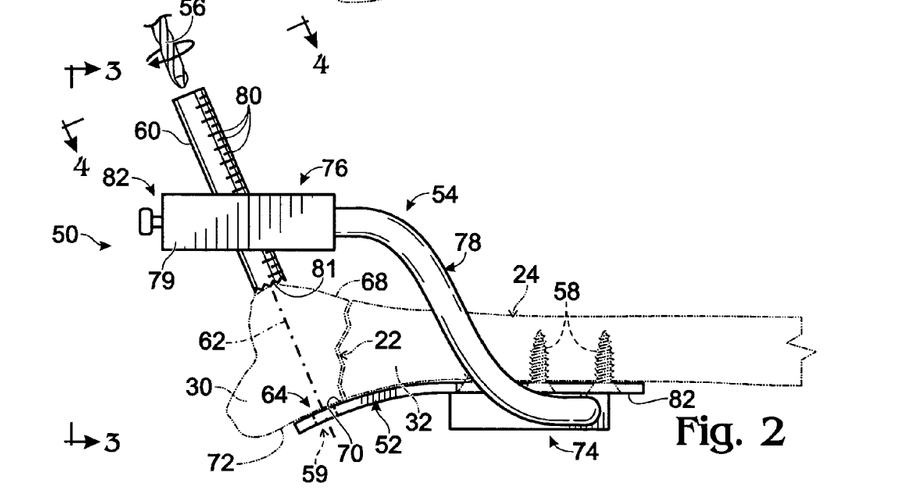
FIG. 2 is a side elevation view of an exemplary guide system disposed on the fractured radius of FIG. 1, with the system including a guide device positioned by a bone plate that is secured to the radius, in accordance with aspects of the invention.

FIG. 2 shows an exemplary guide system 50 positioned on fractured radius 24, with the Colles' fracture 22 reduced. Guide system 50 may include (1) a bone-repair device, such as bone plate 52, (2) a guide device 54, (3) a hole-forming tool 56, and/or (4) a plurality of fasteners 58, among others. The bone-repair device may be connected to guide device 54, to facilitate positioning of the guide device in correspondence with the bone-repair device.

II. Bone-Repair Device

Bone-repair device 52 may include among others any device configured to be attached to one or more bones for repair of the bone(s). The bone-repair device may be an addition to the bone(s) (such as a bone plate), and/or it may be a replacement for a portion or all of the bone(s) (such as a prosthesis), among others. The bone-repair device may be placed in apposition to a natural and/or an engineered surface of the bone(s), such as a cut surface, among others.

The bone-repair device may include one or more openings (such as through-holes, recesses, and/or concavities, among others). In some embodiments, the bone-repair device may include different openings configured to receive fasteners from opposing directions. The opposing directions may direct fasteners (1) through a bone and then to the bone-repair device, and (2) through the bone-repair device and then into the bone. The openings may be threaded or nonthreaded. In some embodiments, threaded openings, nuts, and/or the equivalent may be used for connection of the bone-repair device to fasteners directed from a generally opposing surface of a bone, and threaded (locking or fixed-angle) and/or nonthreaded (nonlocking or variable-angle) openings may be used for directing fasteners through the bone-repair device and then into bone. The threaded or nonthreaded openings may include or lack counterbores.

The bone-repair device may have any suitable configuration for repairing a bone. The bone-repair device may be configured to be attached temporarily to a bone, for any suitable period of time, or attached permanently. In some embodiments, the bone-repair device may be configured for use on both sides of the body or on only the left or right side of the body. When configured as a bone plate, the bone-repair device may be any plate configured to span a bone discontinuity, such as a fracture, an excision, and/or a joint, among others, to fix the relative positions of bone portions or bones on opposing sides of the discontinuity. When configured as a prosthesis, the bone-repair device may be configured to replace an articulating surface or a portion of the articulating surface. Further aspects of bone plates and prostheses that may be suitable for using in the guide system are included in the following patent applications, which are incorporated herein by reference in their entirety for all purposes: U.S. patent application Ser. No. 10/716,719, filed Nov. 19, 2003, titled ADJUSTABLE BONE PLATES, and naming Randall J. Huebner and Steven P. Horst as inventors; U.S. patent application Ser. No. 10/717402, filed Nov. 19, 2003, titled DEFORMABLE BONE PLATES, and naming Randall J. Huebner as inventor; U.S. patent application Ser. No. 10/717,015, filed Nov. 19, 2003, titled BONE PLATES WITH SLOTS, and naming Randall J. Huebner as inventor; U.S. patent application Ser. No. 10/717,399, filed Nov. 19, 2003, titled BONE PLATES WITH REFERENCE MARKS, and naming Randall J. Huebner as inventor; U.S. Provisional Patent Application Ser. No. 60/512,111, filed Oct. 17, 2003; and PCT Patent Application Ser. No. PCT/US02/18623, filed Jun. 10, 2002.

The bone-repair device may include one or more connective features 59. The connective features may be any structure of the bone-repair device that permits coupling of the bone-repair device to a fastener. Accordingly, a connective feature may be a threaded opening to be engaged by a threaded fastener, a nonthreaded opening, a hook, a pin, or the like.

III. Guide Devices

The guide device may play a number of roles. For example, the guide device may (1) apply a force on a bone (or bone fragment) toward a bone plate to reduce a fracture and/or hold the bone in position during fixation; (2) guide a hole-forming tool (for example, a drill bit) into a bone toward a connective feature (such as an opening) of a bone-repair device; (3) measure a distance corresponding to the spacing between the bone-repair device and a guide portion of the guide device, for example, to facilitate fastener selection; and/or (4) direct a bone fastener into a bone so that the distal end of the fastener is received by the connective feature of the bone-repair device, among others. In some embodiments, the guide device may direct threaded fasteners at an angle that allows proper threaded engagement with threaded openings of the bone-repair device.

Guide device 54 may include one or more guide elements 60 that define a path or guide axis 62 for fastener placement. The guide device may define the path or guide axis at least substantially external to the bone, that is, without entering into the bone and/or without passing through the bone. Each guide axis may intersect a predefined position 64 of a bone-repair device, for example, a connective feature 59 (such as an opening) of the bone-repair device. The guide device may guide hole-forming tool 56 and/or a suitable fastener along the guide axis toward predefined position 64 from a generally opposing surface 68 of the bone, and toward a bone-facing or inner surface 70 of the bone-repair device and an adjacent surface 72 of the bone. The guide element, although spaced from a bone-repair device by intervening bone, may be configured so that it may be positioned in alignment with one or more connective features 59 of the bone-repair device, by connection of the bone-repair device to the guide device. The alignment may not only intersect the connective feature but may direct the fastener at a suitable angle for coupling, such as for threaded engagement with a threaded opening.

The guide device may be formed of any suitable material(s), particularly rigid materials. Suitable materials for the guide device may include metal or a metal alloy, a biocompatible material (stainless steel, a titanium alloy, cobalt chromium, etc.), a ceramic, wood, plastic, glass, and/or the like.

The guide device may be configured for use with a particular bone-repair device and/or a set of such devices. Accordingly, the guide device may be configured in correspondence with a bone-repair device for use on both sides of the body or for use on only the right or left side of the body.

The guide device may include, among others, (1) a coupling portion 74, (2) a guide portion 76, and/or (3) an optional spacer portion 78, connecting the coupling and guide portions, for example, as described below.

i. Coupling Portion

Coupling portion 74 may include among others any structure configured to provide coupling or connection of the guide device to the bone-repair device. The coupling portion may provide coupling to a predetermined position(s) of the bone-repair device. Accordingly, the coupling portion may include openings and/or fasteners (such as screws, clips, pins, etc.) that position the coupling portion relative to and/or connect the coupling portion to the bone-repair device. For example, a coupling mechanism may include a snap-fit engagement of complementary structures on the guide portion and bone-repair device, clasps that attach the guide portion to the bone-repair device, a clamp-like engagement with the bone-repair device, attachment with one or more threaded fasteners, and/or the like. In some embodiments, the bone-repair device may be configured to include dedicated features (such as openings, ridges, protrusions, indentations, etc.) provided only for use with the coupling portion. Alternatively, openings or other features of the bone-repair device may be used for attachment to the coupling portion and also for attachment to a bone after the coupling portion has been disconnected from the bone-repair device. Whatever the mechanism of connection, the connection should be sufficiently stable so that the guide portion does not detach unexpectedly as it performs a selected guide function. The coupling portion may be connected to a bone-repair device before or after the bone-repair device is connected to a bone.

The coupling portion may be connected to any suitable portion of a bone-repair device. For example, the coupling portion may be connected an axial portion or a transverse portion of a bone plate. Furthermore, the coupling portion may be connected to a fixed or movable portion of a bone-repair device. For example, the coupling portion may be connected to first portion of a bone plate that is movable pivotally or translationally (through a mechanical joint or deformable region) in relation to a second portion of the bone plate. The second portion may be fixed to bone or adjustably positionable thereon, such as with slots in which bone screws are received but not fully tightened into bone. In some embodiments, the first portion may be an axial plate portion and the second portion may be a transverse plate portion. Further aspects of adjustable or movable bone plates to which the coupling portion may be connected are described in the following patent applications, which are incorporated herein by reference in their entirety for all purposes: Ser. No. 10/716,719, filed Nov. 19, 2003, titled ADJUSTABLE BONE PLATES, and naming Randall J. Huebner and Steven P. Horst as inventors; Ser. No. 10/717, 402, filed Nov. 19, 2003, titled DEFORMABLE BONE PLATES, and naming Randall J. Huebner as inventor; Ser. No. 10/717,015, filed Nov. 19, 2003, titled BONE PLATES WITH SLOTS, and naming Randall J. Huebner as inventor; and U.S. patent application Ser. No. 10/717.399, filed Nov. 19, 2003, titled BONE PLATES WITH REFERENCE MARKS, and naming Randall J. Huebner as inventor.

ii. Guide Portion

Guide portion 76 may include among others any structure connected to coupling portion 74 and configured to define guide axis 62. The guide axis may be any path along which a tool or fastener may be guided physically by the guide portion. Accordingly, the guide axis may be defined by a guide element 60 having a passage, such as a channel, through which a tool or fastener may be advanced axially. The passage may restrict substantial lateral movement of the tool or fastener by having a diameter slightly larger than a tool and/or fastener for which the passage is configured. The guide element may be an integral component of the guide portion, such as an aperture or opening formed in the guide portion, or may be formed by a separate component, such as a tube (or cannula) of any suitable shape and size disposed in a frame 79 of the guide portion. The tube may direct a drill bit, a fastener (such as a bone screw), and/or a driver (such as screwdriver), among others, through the guide element and along guide axis 62 through intervening bone and then to an oppositely situated bone-repair device.

The guide portion may define any suitable number of guide axes and may include any suitable number of guide elements. In some embodiments, the guide portion may define a set of two or more guide axes that intersect a corresponding set of two or more connective features, such as threaded openings, of the bone-repair device. A guide element may be movable to spaced positions within the frame to define spaced guide axes of a guide portion.

Alternatively, or in addition, the coupling portion may be movable relative to the frame and/or bone repair device to define spaced guide axes.

Guide portion 76 may have any suitable structural relationship to coupling portion 74 and target bone. The guide and coupling portions may be joined as a single piece or may be formed by distinct components. Guide portion, particularly frame 79, may have any suitable clearance relative to a target bone. For example, the clearance may be about 0.5" to 2" to avoid contact with soft tissue disposed over the target bone and/or to provide for variations in bone size within the population.

Guide element 60 may be fixed or movable relative to the coupling portion and may be fixedly or movably disposed within guide portion 76. In some embodiments, a guide element may be movable laterally to a plurality of predefined positions within frame 79. Alternatively, or in addition, a guide element may be movable axially to adjust its spacing from the bone-repair device. For example, a guide element may be movable axially, as the frame of the guide portion remains fixed.

Indicia of the guide device may be configured to correspond to the spacing between guide element 60 and a bone-repair device. For example, the indicia may include graduations 80 and/or symbols disposed in, on, and/or about the guide element, among others. Such indicia may be configured to report a distance between the guide element and an oppositely situated bone-repair device. For example, the distance may be measured from a distal end 81 of guide element 60 to bone plate 52, and thus may relate to the relationship of the guide element to frame 79. Sets or arrays of indicia may be arrayed generally parallel to guide axis 62 and may include symbols (such as numbers) that correspond to the distance measured. A fixed feature on frame 79 may identify an indicium, such as a particular graduation, that corresponds to the measured distance, for example, the first graduation visible above or below frame 79, among others. By knowing this distance, a surgeon may select a fastener of sufficient length to span intervening bone and extend into effective engagement with the bone-repair device.

In some embodiments, guide element 60 may have restricted movement in one or both directions parallel to guide axis 62. Restricted movement of guide element 60 may be governed by a detent mechanism 82. The detent mechanism may be any mechanism configured to restrict movement of a guide element relative to the coupling portion and/or other regions of the guide portion. In some embodiments, the detent mechanism may permit axial movement of guide element 60 toward the bone-repair device, but restrict axial movement away from the bone-repair device. This may permit a guide element to apply a force on a bone (or bone portion) toward a bone-repair device, for example, parallel to a guide axis, to urge the bone (or portion) toward the bone-repair device. The detent mechanism also may be releasable to permit axial movement of the guide element in both directions.

iii. Spacer Portion

The guide portion may be connected to the coupling portion by a spacer portion 78. The spacer portion may be any structure that connects a coupling portion to a guide portion of a guide device, so that these portions are disposed adjacent spaced positions of a generally convex bone surface, generally at predefined relative positions. The spacer portion may be configured to extend adjacent any suitable surface of a bone. Accordingly, the spacer portion may be bent, arcuate, helical, and/or angular, among others. In some embodiments, the spacer portion may extend along a convex bone surface, to provide a connection of the guide portion to the coupling portion that is external to bone. For example, the spacer portion may extend between generally opposing surfaces of a bone. Generally opposing bone surfaces, as used herein, are spaced bone surface regions that can be spanned by a fastener passing through bone. The spacer portion may extend, for example, around the medial, lateral, dorsal, ventral, rostral, and/or caudal side of a target bone, as appropriate for the target bone. When configured for use with a distal radius fracture, the spacer portion may be configured to extend around either side of the radius, for example, the medial side.

The spacer portion may be rigid and may be fixed in position relative to the other portions of the guide device. However, in some embodiments, the spacer portion (and/or the guide portion) may be movable incrementally or continuously, for example, to guide fasteners to distinct connective features of a bone-repair device, to guide fasteners to different bone-repair devices, and/or to make small adjustments in the alignment of the guide portion. This movement may be rotary and/or translational, as determined by joints within the spacer portion or between the spacer portion and the coupling and/or guide portions.

IV. Hole-Forming Tools

Hole-forming tool 56 may include among others any manually and/or power-driven tool that can remove bone material from along and/or about the guide axis to create a hole. The tool may be a drill with a drill bit, a reamer, a punch, and/or the like. In some embodiments, the tool may be a fastener that is configured to be self-drilling, such as a self-drilling bone screw. The hole may be a through-hole extending completely through a bone, between generally opposing surfaces of the bone. The hole may include a counterbore to receive a head of a fastener.

V. Fasteners

Fastener 58 may include among others any structure configured to couple a bone-repair device to a bone. The fastener may be a bone screw, a wire, a pin, and/or the like. The fastener may be configured to engage a bone and the bone-repair device using a head and/or a shaft of the fastener. For example, the fastener may be a "type 1" or a "type 2" bone screw. Type 1 bone screws are configured to be received by a bone-repair device from an inner surface of the device after traveling through a bone. Type 2 bone screws are configured to be received by the bone-repair device from an outer surface of the device. Accordingly, type 1 screws may include a threaded shaft that is complementary to a threaded opening included in the bone-repair device and/or a structure such as a nut associated therewith. By including threaded openings in the bone-repair device, a fastener may be rotated into threaded engagement with the bone-repair device at the distal (or proximal) end of the fastener. A proximal end or head of the fastener may engage the bone (or bone fragment) at an opposing surface of the bone (a natural or engineered surface, such as a recessed surface), so that the bone-repair device and bone are pulled toward one another.

VI. EXAMPLES

The following examples describe selected aspects and embodiments of the invention, including, among others, exemplary guide systems, and methods of use thereof, for repairing fractures of the distal radius. These examples are included for illustration and are not intended to limit or define the entire scope of the invention.

Example 1

Exemplary Guide System I

This example describes further aspects of guide system 50; see FIGS. 3–7. The same reference indicators are used to refer to the same system components throughout the discussion of FIGS. 1 and 2 above and FIGS. 3–7 below. Thus, to make it easier to understand the relationship between different drawings, selected drawings may include reference indicators for system components that are discussed primarily or exclusively in the context of other drawings.

Figure 3:
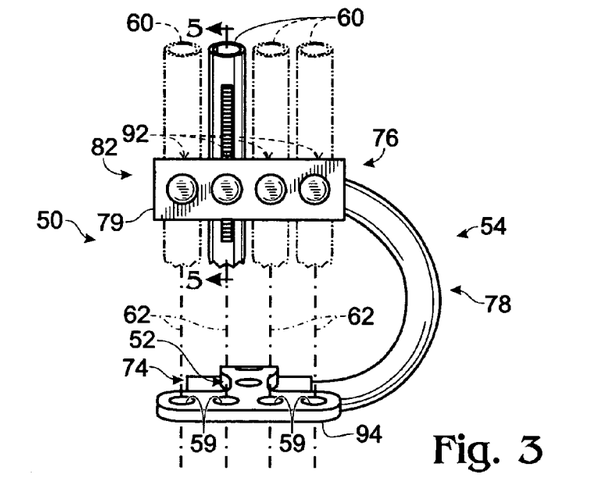
FIG. 3 is an end view of the guide system of FIG. 2 in the absence of bone, viewed generally along line 3—3 of FIG. 2.

FIG. 3 shows an end view of guide system 50 from FIG. 2, in the absence of radius 24, viewed generally along line 3—3 of FIG. 2. Guide system 50 may be configured to define a plurality of guide axes 62. The guide axes may intersect corresponding connective features of bone plate 52, such as a spaced set of threaded openings 59. Threaded openings 59 may be arrayed in a linear or nonlinear configuration, as appropriate.

Guide portion 76 may define guide axes 62 using a guide element 60 that is removable from the guide portion. Accordingly, a single guide element 60 may be moved among a plurality of receiving sites 92 defined by frame 79 of the guide portion. The receiving sites may be configured, for example, as bores or openings in frame 79 (see FIG. 4). In the present illustration, guide element 60 occupies one of the receiving sites; alternative lateral positions of the guide element are indicated in phantom outline. In alternative embodiments, the guide portion may include a plurality of guide elements 60, such as a guide element for each receiving site 92 of the frame.

Guide device 54 may be connected to bone plate 52 so that bone-opposing or outer surface 94 of the bone plate is apposed to the guide device (see also FIG. 2). Accordingly, coupling portion 74 may be spaced from a target bone by bone plate 52. Outer surface 94 may oppose inner surface 70 of the bone-repair device, so that the inner surface is disposed closer to the guide portion of the guide device.

Figure 4:
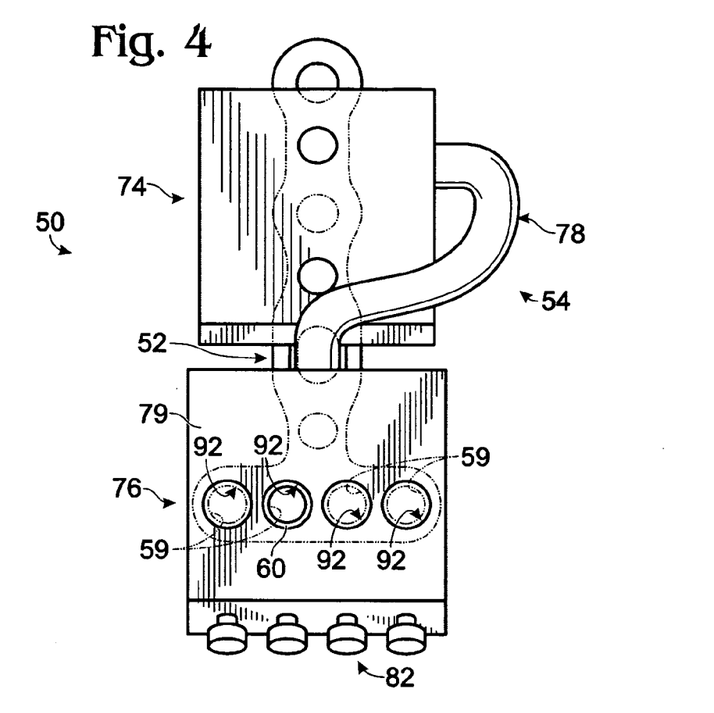
FIG. 4 is a top view of the guide system of FIG. 2 in the absence of bone, viewed generally along line 4—4 of FIG. 2.

FIG. 4 shows a top view of guide system 50 from FIG. 2, in the absence of radius 24. Coupling portion 74 and spacer portion 78 position guide portion 76 in correspondence with bone plate 52. In particular, receiving sites 92 are aligned with threaded openings 59 of the bone plate, so that guide element 60, when suitably positioned in each receiving site, may guide a bone screw into each opening 59.

Figure 5:
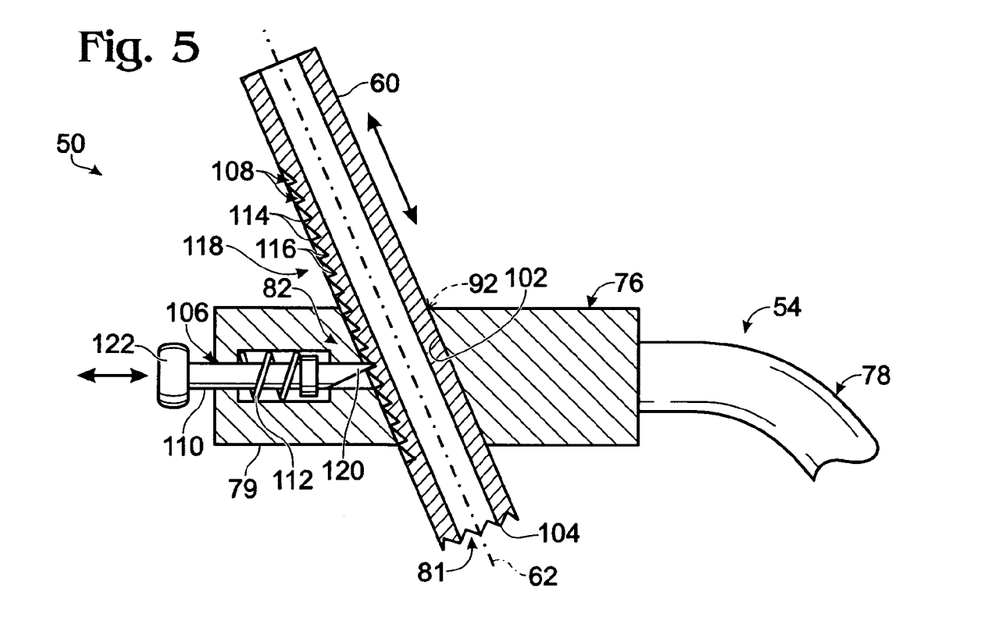
FIG. 5 is a sectional fragmentary view of the guide system of FIG. 2, viewed generally along line 5—5 of FIG. 3.

FIG. 5 shows a sectional view of selected portions of guide device 54, particularly guide portion 76. Guide element 60 may be received slidably in a bore 102 defining receiving site 92. Bore 102 may define the angular disposition of guide element 60 and sliding movement thereof. Distal end 81 of the guide element may include one or a plurality of projections 104, to create a serrated end structure that engages a bone and restricts lateral bone movement when the guide element is moved into contact with the bone along guide axis 62.

Detent mechanism 82 may be configured to allow or restrict movement of guide element 60. The detent mechanism may include a movable catch 106 and an array of engagement sites 108 for the catch. The catch may be configured, for example, as a pin 110 that is biased in position using a biasing mechanism, such as spring 112. Engagement sites 108 may be defined by a series of projections 114 and/or depressions 116, for example, forming a set of teeth 118. Teeth 118 and/or a distal end 120 of the pin may be configured to be asymmetric in profile, so that movement of guide element 60 away from the bone is restricted and movement toward the bone is permitted. Pin 110 may be movable within frame 79 between engaged and released positions. In the engaged position, shown in the present illustration, distal end 120 of the pin may engage teeth 118 to restrict movement of guide element 60 away from the bone, parallel to guide axis 62, but to permit movement of the guide element toward the bone. Pin 110 also may include a handle 122 that may be operated with a tool or manually, without tools, to move pin 110 out of engagement with teeth 118, thereby releasing guide element 60 so that it is permitted to slide in one or both axial directions.

In operation, guide element 60 may be moved into engagement with a bone so that serrated distal end 81 applies a force on the bone. The force may be directed toward bone plate 52. Thus, guide element 60 and bone plate 52 may form a clamp that holds a bone fragment or portion in position between the guide portion and the bone plate. Detent mechanism 82 may be inactivated, such as by retraction of pin 110, to release the clamp, which may permit movement of the guide element away from the bone, thus releasing intervening bone.

Figure 6:
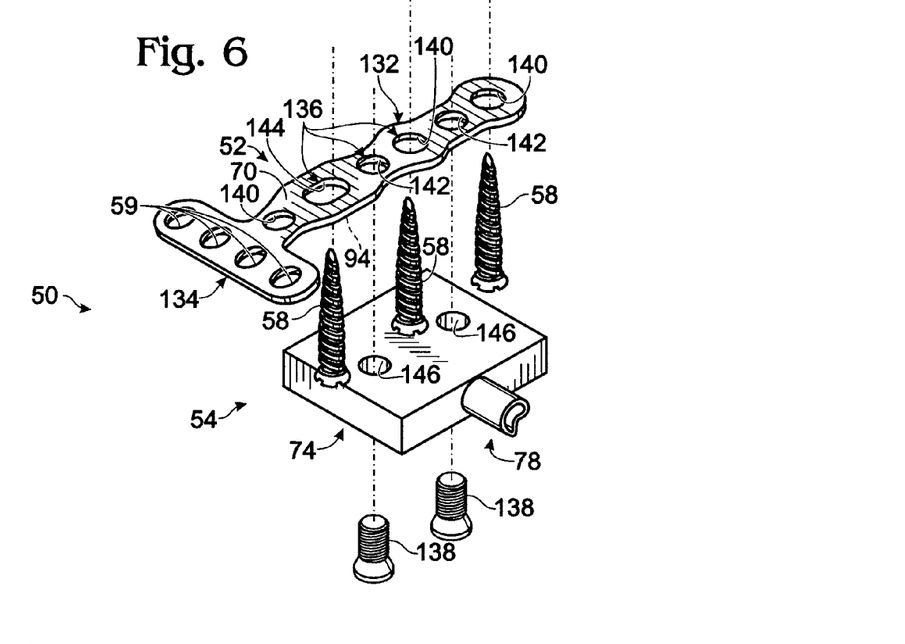
FIG. 6 is an exploded view of a portion of the guide system of FIG. 2.

FIG. 6 shows an exploded view of a volar portion of guide system 50. An exemplary placement of screws into an axial region 132 of bone plate 52 is indicated. The bone plate may be generally T-shaped. Accordingly, axial region 132 may be joined to a transverse region 134 of the bone plate. The axial region may be configured to be attached to a major portion of a fractured bone, aligned with its long axis at least substantially parallel to the axis of the bone. The axial region may be longer than the transverse region, about the same length as the transverse region, or shorter than the transverse region, as appropriate for a particular application. Axial region 132 may include a plurality of connective features 136 to receive fasteners such as type 2 bone screws 58 and machine screws 138. The connective features may be openings 140, 142, 144, as shown here, or cavities, among others. Openings may be circular, shown at 140, 142, and/or slots, shown (as a compression slot) at 144. The connective features may be independently threaded, partially threaded, or nonthreaded. In the present illustration, openings 142 are threaded, and openings 140, 144 are nonthreaded.

Transverse region 134 may be configured to be attached to an end region of the bone, such as to a bone fragment produced by a fracture. The transverse region may provide a wide support platform to stabilize the bone fragment.

Screws may be placed through openings 140–144 to connect bone plate 52 to the bone and the guide device to the bone plate. For example, one or more of bone screws 58 may be placed through openings 140, 144 from bone-opposing surface 94 and into bone. In addition, one or more machine screws may be placed through bores 146 of coupling portion 74 for engagement with threaded openings 142 of the bone plate. In some embodiments, bone plate openings for connection of the guide device to the bone plate may be nonthreaded, so that guide device 54 is connected to the bone plate via underlying bone. In some embodiments, the bone plate may be configured for attachment of the guide device to the transverse portion of the plate. The transverse portion may be fixed or adjustably positionable in relation to the axial portion of the plate.

Figure 7:
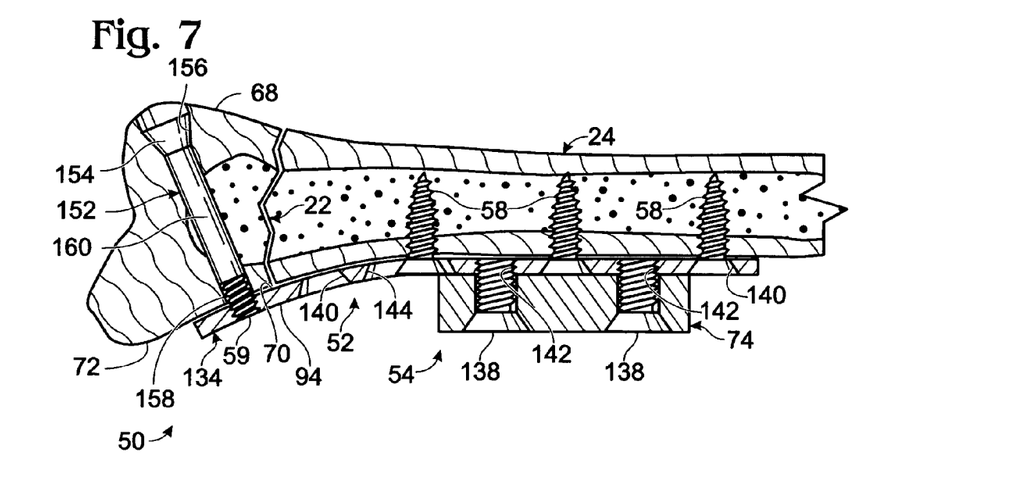
FIG. 7 is a sectional view of the distal right radius of FIG. 1, after bone fixation using the guide system of FIG. 2, in accordance with aspects of the invention.

FIG. 7 shows a sectional view of distal right radius 24 after fixation using guide system 50. Bone screws 58 may be configured to received unicortically or bicortically in radius 24 and from opposing directions of approach toward the bone plate.

Some bone screws may attach the bone plate to the bone by passing first through the plate and then into or through the bone. In such embodiments, bone screws 58 disposed more distally on the bone may be shorter, unicortical screws. The use of unicortical screws distally may minimize the chance that the distal ends of the screws protrude dorsally to irritate tendons. Conversely, bone screws disposed more proximally on the bone may be longer, bicortical screws, to improve anchorage to the radius in this region. In some embodiments, the axial portion of the bone plate may include staggered openings that direct bone screws along nonparallel paths to achieve better purchase on bone, so that shorter bone screws may be used. Further aspects of bone plates with staggered openings that may be suitable for use with the guide device are included in the following patent application, which is incorporated herein by reference: U.S. Provisional Patent Application Ser. No. 60/512,111, filed Oct. 17, 2003.

Alternatively, or in addition, some bone screws may attach the bone plate to the bone by passing first through the bone and then into the plate. For example, one or more opposing screws 152 may be received by bone plate 52 from opposing surface 68 of the radius and from bone-facing surface 70 of the bone plate. Opposing screws 152 may be received by transverse region 134 of the bone plate (and/or axial region 132 (see FIG. 6)). A head 154 of an opposing screw may engage a natural opposing surface 68 of bone or a recessed surface 156 created from the natural opposing surface. A threaded shaft 158 disposed distally to head 154 may be configured to engage threaded openings 59. Intermediate region 160 of the shaft may be threaded or nonthreaded. The intermediate region may have any suitable diameter. However, in some embodiments, the intermediate region may be configured so that it cannot be received in a threaded connective feature of a bone-repair device. In these embodiments, advancement of the screw stops when the intermediate region reaches the connective feature. Such a configuration of the intermediate region may prevent excessive protrusion of the distal end of the screw above the outer surface 94 of the bone-repair device. Accordingly, the intermediate region of the screw may define a shoulder of greater diameter (threaded or nonthreaded) and/or may have a thread structure that is not complementary to threads of a corresponding connective feature. The overall lengths of opposing screws, and particularly the shafts of such screws, may be selected to correspond generally to the thickness of the bone and bone-repair device into which the shafts extend. Threaded engagement of a bone screw with a bone plate may help to fix the angle with which the screw extends into a bone fragment, thereby reducing any movement of the bone fragments permitted by movement of the bone screw relative to the bone plate.

Finally, some screws such as machine screws 138 may be used to attach guide device 54 to bone plate 52 and position the guide device thereon, without contacting or penetrating into the bone.

Example 2

Exemplary Guide System II

Figure 8:
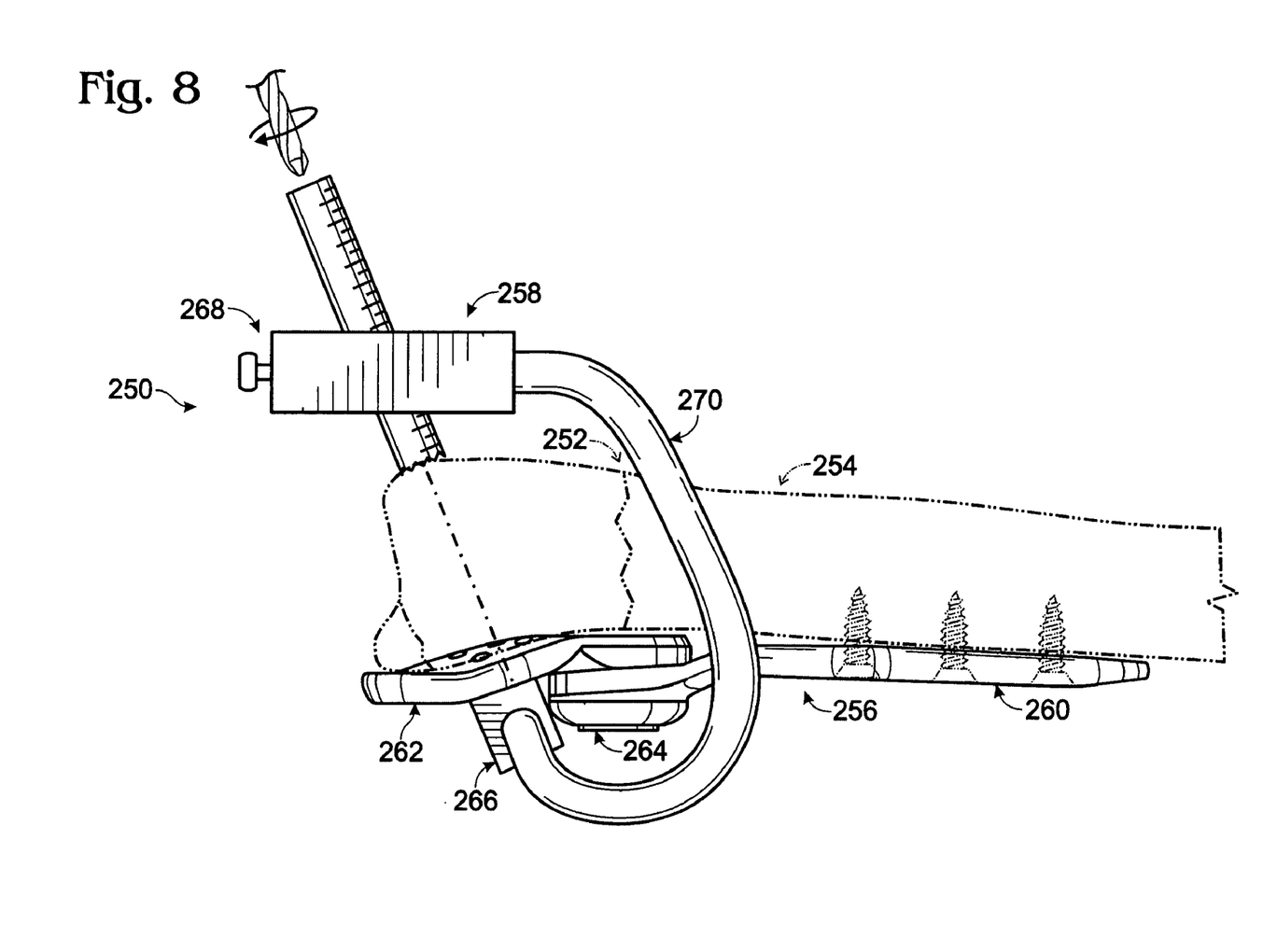
FIG. 8 is a side elevation view of an alternative exemplary guide system disposed on a fractured radius, in accordance with aspects of the invention.

This example describes another exemplary guide system; see FIG. 8.

Guide system 250 may be configured to fix a fracture 252 of distal radius 254. Guide system 250 may include an adjustable bone plate 256 and a guide device 258, among others.

Adjustable bone plate 256 may include a proximal anchor portion 260, a distal anchor portion 262, and a joint 264 connecting the anchor portions. The joint may permit pivotal and/or translational movement of the anchor portions relative to each other. In the present illustration, joint 264 permits pivotal movement about three orthogonal axes. The joint may have an adjustable configuration, in which adjustment is permitted, and a fixed configuration, in which the relative disposition of the anchor portions is fixed.

Guide device 258 may be configured generally as described above in Section I for guide device 54. Accordingly, the guide device may include a coupling portion 266, a guide portion 268, and a spacer portion 270 connecting the coupling and guide portions. Coupling portion 266 may be configured to be connected to distal anchor portion 262 of the bone plate, so that adjustment of distal anchor portion 262 is coupled to adjustment of guide portion 268. In particular, a change in the angular disposition of guide portion 268 may create a corresponding change in the angular disposition of distal anchor portion 262. Thus, any portion of the guide device may be used as a handle, which may be grasped by a user's hand, to produce corresponding changes in the disposition of guide portion 268 and the distal anchor portion 262.

Further aspects of adjustable bone plate 256 and other adjustable bone plates that may be used in the guide systems described here, are included in the following patent applications, which are incorporated herein by reference: U.S. patent application Ser. No. 10/716,719, filed Nov. 19, 2003, titled ADJUSTABLE BONE PLATES, and naming Randall J. Huebner and Steven P. Horst as inventors; U.S. patent application Ser. No. 10/717,402, filed Nov. 19, 2003, titled DEFORMABLE BONE PLATES, and naming Randall J. Huebner as inventor; U.S. patent application Ser. No. 10/717,015, filed Nov. 19, 2003, titled BONE PLATES WITH SLOTS, and naming Randall J. Huebner as inventor; and U.S. patent application Ser. No. 10/717,399, filed Nov. 19, 2003, titled BONE PLATES WITH REFERENCE MARKS, and naming Randall J. Huebner as inventor.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A system for bone fixation, comprising:
    a bone plate structured to be secured to a bone such that the bone plate covers an exterior surface region of the bone, the bone, plate including a connective feature; and
    a guide device including a guide portion and being structured to attach to the bone plate and to extend around the bone from the bone plate such that the guide portion opposes the bone plate across the bone and defines a guide axis for the connective feature of the bone plate.

2. The system of claim 1, wherein the bone plate includes an inner surface that faces the bone and an outer surface that opposes the inner surface, and wherein the guide portion is disposed closer to the inner surface than the outer surface.

3. The system of claim 1, wherein the connective feature is a threaded opening.

4. The system of claim 3, the threaded opening being a plurality of threaded openings included in the bone plate, wherein the guide portion is configured to guide fasteners through the bone and then to each of the threaded openings.

5. The system of claim 1, wherein the guide portion includes a frame and a guide element coupled movably to the frame, and wherein the guide element defines the guide axis.

6. The system of claim 5, wherein the guide element is movable parallel to the guide axis.

7. The system of claim 6, wherein the guide element includes indicia configured to measure a distance along the guide axis, and wherein the distance corresponds to a spacing of the bone plate from the guide element.

8. The system of claim 5, wherein the bone plate includes a plurality of predefined positions, and wherein the guide element is movable to define guide axes intersecting each of the predefined positions.

9. The system of claim 5, wherein the guide portion includes a detent mechanism configured to restrict movement of the guide element.

10. The system of claim 9, wherein the detent mechanism is configured to permit movement of the guide element toward the bone and to restrict movement of the guide element away from the bone.

11. The system of claim 9, wherein the detent mechanism is configured to be releasable manually without tools.

12. The system of claim 1, wherein the guide portion is configured to be movable into engagement with the bone so that the bone is pushed toward the bone plate.

13. The system of claim 1, wherein the guide portion includes a removable cannula defining the guide axis.

14. The system of claim 1, wherein the bone is a radius bone, and wherein the bone plate is configured to be connected adjacent a distal volar surface of the radius bone.

15. The system of claim 1, wherein the bone plate and the guide device are configured in correspondence for use on a left side or a right side of a body, but not both.

16. The system of claim 1, wherein the guide device extends only to an opposing side of the bone from the bone plate when the bone plate is secured to bone and the guide device is attached to the bone plate.

17. The system of claim 1, wherein the guide device extends about half way around the bone from the bone plate when the bone plate is secured to bone and the guide device is attached to the bone plate.

* * * * *